United States Patent
Linders et al.

(10) Patent No.: US 9,320,211 B2
(45) Date of Patent: Apr. 26, 2016

(54) BRASSICA PLANTS RESISTANT TO DISEASE

(75) Inventors: Enrico Gerardus Albertus Linders, Enkhuizen (NL); Thaam Wijnker, Enkhuizen (NL); William Briggs, Enkhuizen (NL); Sjaak Van Der Ploeg, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 987 days.

(21) Appl. No.: 13/497,746

(22) PCT Filed: Sep. 19, 2010

(86) PCT No.: PCT/EP2010/063761
§ 371 (c)(1),
(2), (4) Date: Mar. 22, 2012

(87) PCT Pub. No.: WO2011/036108
PCT Pub. Date: Mar. 31, 2011

(65) Prior Publication Data
US 2012/0185960 A1    Jul. 19, 2012

(30) Foreign Application Priority Data
Sep. 22, 2009  (EP) .................................... 09171021

(51) Int. Cl.
*A01H 5/00* (2006.01)
*C12Q 1/68* (2006.01)

(52) U.S. Cl.
CPC ............... *A01H 5/00* (2013.01); *C12Q 1/6895* (2013.01); *C12Q 2600/13* (2013.01); *C12Q 2600/156* (2013.01); *C12Q 2600/172* (2013.01)

(58) Field of Classification Search
None
See application file for complete search history.

(56) References Cited

FOREIGN PATENT DOCUMENTS

| WO | 2004/013334 | 2/2004 |
| WO | 2008/133503 | 11/2008 |
| WO | WO 2008133503 A1 * | 11/2008 |

OTHER PUBLICATIONS

Collard et al. (Euphytica, (2005), 142: pp. 169-196).*
Santos M R et al: "Evaluation of a core collection of Brassica oleracea accessions for resistance to white rust of crucifers (*Albugo candida*) at the cotyledon stage", Genetic Resources and Crop Evolution, Kluwer Academic Publishers, DO, vol. 51, No. 7, Nov. 1, 2004, pp. 713-722.
Leckie D. et al: "Variation for response to *Peronospora parasitica* (downy mildew) and *Albugo candida* (white blister) in brassica and Arabidopsis", Acta Hort. (IHIS), No. 407, 1996, pp. 447-452.
Leckie D. et al: "Differential resistance to peronospora and albugo candida in Brassican oleracea", Acta Hort. Proc. Intl. Symp. on Brassicas, vol. 459, 1998, p. 357.
Farinho M et al: "Mapping of a locus for adult plant resistance to downy mildew in broccoli (*Brassica oleracea* convar. italica)", Theoretical and Applied Genetics, vol. 109, No. 7, Nov. 2004, pp. 1392-1398.
Kole C et al: "Molecular mapping of a locus controlling resistance to Albugo candida in Brassica rapa", Phytopathology, vol. 86, No. 4, 1996, pp. 367-369.

* cited by examiner

*Primary Examiner* — David T Fox
*Assistant Examiner* — Jared Shapiro
(74) *Attorney, Agent, or Firm* — Karen A. Magri

(57) ABSTRACT

The present invention relates to novel *Brassica oleracea* plants resistant to *Albugo candida* and the seeds of said plants. The invention also relates to methods of making such plants and for producing seeds thereof. The invention further relates to molecular markers and use thereof in marker assisted breeding and for identifying *Albugo candida* resistance trait in *Brassica oleracea* plants.

13 Claims, No Drawings

US 9,320,211 B2

BRASSICA PLANTS RESISTANT TO DISEASE

This application is a 371 of International Application No. PCT/EP2010/063761 filed Sep. 19, 2010, which claims priority to EP 09171021.0 filed Sep. 22, 2009, the contents of which are incorporated herein by reference.

The present invention relates to novel plants resistant to *Albugo candida* and the seeds of said plants. The invention also relates to methods of making such plants and for producing seeds thereof. The invention further relates to markers and use thereof in marker assisted breeding and for identifying *Albugo candida* resistance trait.

*Albugo candida* (syn.: *A. cruciferum* also called white rust) or *Albugo candida* occurs in all parts of the world where cruciferous crops are grown.

*Albugo candida* is a widespread disease that causes serious problems in many *Brassica* growing areas.

White rust most commonly occurs on: field mustard (*Brassica campestris* L.), leaf or Chinese mustard (*B. juncea* Zerj, & Coss.), black mustard (*B. nigra* (L.) Koch), broccoli (*B. oleracea* L. var. *italica* L.), cauliflower (*B. oleracea* L. var. *botrytis* L.), cabbage (*B. oleracea* L. var. *capitata* L.), Brussels sprouts (*B. oleracea* L. var. *gemmifera* DC), Chinese or celery cabbage (*B. pekinensis* (Lour.) Rupr.), rutabaga (*B. campestris* L. var. *napoBrassica* (L.) DC.), pak-choi (*B. chinensis* L.), turnip (*B. rapa* L.), radish (*Raphanus sativus* L.), and daikon (*R. sativus* L. var. *longipinnatus* Bailey).

Sporangia are produced in pustules and once liberated, are dispersed by wind, rain, or insects to neighbouring plants. The sporangia require some drying in order to germinate well. Each germinating sporangium gives rise to five to seven zoospores. The preferred temperature for germination ranges from 1 to 18° C., but is optimum between 10 and 14° C. Temperatures should be between 16 and 25° C., with the optimum at 20° C. for zoospores to produce germ tubes and penetrate plant tissue. The moisture necessary for zoospore activity is ideal when in the form of heavy dew or fog or during periods of extended rainfall and lower temperatures. (Vanterpool, T. C. 1959. *Oospore germination in Albugo candida. Can. J. Bot.* 37:169-172).). Although *A. candida* shows specialization to specific hosts, the disease seems to develop under similar conditions over a wide range of isolates and hosts (Gilijamse et al., 2004, Spencer, Philips and Jeger (eds.), Advances in Downy mildew Research, Vol. 2, p. 107-118).

In contrast to other *Brassica* crops, oospores seem not to play a significant role in the epidemiology of *B. oleracea* crops as no oospores have been reported yet. Asexual reproduction and survival of sporangia on year-round production of *B. oleracea* crops does not necessitate oospores to be formed for survival during crop free periods. (Gilijamse et al., 2004, Spencer, Philips and Jeger (eds.), Advances in Downy mildew Research, Vol. 2, p. 107-118).

Santos screened more than 30 *Brassica oleracea* accessions for resistance to *Albugo candida* disease (*Proc. Int. Symp. Brassica s. Ninth Crucifer Genetics Workshop. Acta Hort.* 407. *ISHS* 1996). His conclusions are that the majority of accessions showed susceptibility and among the tested accessions, one or two wild species of *Brassica oleracea* var. *costada* could consist in a source of resistance to explore and improve. In 2004 Santos and Dias screened a core collection of 400 accessions representing the genetic and geographic diversity of *B. oleracea*. Again a great variability of reactions was found between and within accessions of the core collection. Nine accessions presented 50-78% of resistant seedlings and could be considered as potential sources for breeding programs for white rust resistance (*Genetic Resources and Crop Evolution* 51: 713-722, 2004).

Pest management involves preventive and curative measures including chemical treatment. Plowing or disking diseased plants and plant parts results in rapid decomposition of infected tissues and helps to significantly reduce future white rust infection. Crop rotation with noncruciferous host plants is also effective. Weed control and other sanitary methods are necessary too.

Resistance has been studied and successfully deployed with mustard and rutabaga, however, with cultivated *Brassica oleracea* species like broccoli, white cabbage, Brussels sprouts and the like, such resistance has not yet been identified.

The development of the acylalanine fungicide metalaxyl (Ridomil®) improved the ability to control while rust with fungicide application. Metalaxyl provides limited curative activity and some control of systemic infection.

Applications should be made to the soil and subsequently applied to the foliage. Frequency of application would vary according to the length of crop and amount of rainfall experienced. In temperate environments a soil application and a minimum of 1-2 foliar applications during the crop cycle is suggested. In the field, this fungus is difficult to control because it causes infections that remain dormant in the field and develop into fruit decay during post-harvest storage. Crop losses of up to 50% are not uncommon. Strategies for controlling *Albugo candida* are limited by the emergence of strains that are resistant to one or several groups of fungicides. Most fungicides are protective in their action and will not suppress an established infection, which limits effective control to pre-harvest applications of fungicide.

Therefore, good genetic resistance of the crop is important for its protection against the disease.

There was therefore a long felt and unmet need for convenient, efficient and economically sustainable strategies to protect *Brassica* species, especially cultivated *Brassica oleracea* species against *Albugo candida* infestation. Therefore, there is an unfulfilled need for *B. oleracea* cultivated plants with an improved resistance to *Albugo candida*, wherein the resistance is also easy to breed and transfer to commercial *Brassica*, particularly *Brassica oleracea* lines.

The present invention addresses this need by providing a *Brassica* plant, particularly a *Brassica oleracea* plant, and more particularly a cultivated *Brassica oleracea* plant, which is resistant to *Albugo candida* and thus protected from damage caused by this pathogen. The provision of *Albugo candida* resistant *Brassica* plants, especially *Brassica oleracea* plants, is an environmentally friendly alternative for the use of pesticides and may increase the efficiency of biological control options and contribute to successful integrated pest management programs.

The technical problem underlying the present invention is, therefore, the provision of an *Albugo candida* resistant cultivated *Brassica* plant, particularly a cultivated *Brassica oleracea* plant, which shows resistance to this pathogen.

The technical problem is solved by the provision of the embodiments characterized in the claims. Moreover, it was now found within the scope of the present invention that the linkage between genes responsible for undesired, morphological changes at the plant and the gene responsible for the resistance to *Albugo candida* as present in the wild-type source material, could be broken and is, therefore, no longer present in the cultivated *Brassica oleracea* plant according to the invention.

Accordingly, the present invention addresses the problem of unsatisfactory resistance to the disease *Albugo candida* in cultivated *Brassica oleracea*. To achieve improved resistance to the disease in cultivated *Brassica oleracea*, the present invention discloses the transfer of a genetic determinant responsible for monogenic semi-dominant-resistance to *Albugo candida* from a wild source undomesticated *Brassica* species, such as Kale cabbage for example to different cultivated *B. oleracea* species, such as white cabbage, broccoli, cauliflower and Brussels sprouts for example.

The resistance to *Albugo candida* can be transferred by means of hybridization, followed by repeated backcrosses and disease tests in all backcross generations. High level of resistance to *Albugo candida* is obtained in the resulting *B. oleracea* cultivated plants. The resistance is stable, and can be transmitted to further generations and transferred to susceptible or less resistant *B. oleracea* cultivated plants.

Thus, the present invention discloses *Brassica oleracea* cultivated plants resistant to *Albugo candida*, wherein the resistance to *Albugo candida* is monogenic and semi-dominant, including seeds and materials of said cultivated plants and the progeny thereof. The present invention also discloses methods to produce *Brassica oleracea* cultivated plants resistant to *Albugo candida*, methods to transfer the *Albugo candida* resistance to susceptible or less resistant *Brassica oleracea* cultivated plants. The present invention also further discloses molecular markers linked to the resistance to *Albugo candida*.

In a $1^{st}$ embodiment, the invention relates to a cultivated *Brassica oleracea* plant resistant to *Albugo candida*, comprising a resistance locus, such locus being linked to a genetic determinant obtainable from the genome of a wild *Brassica oleracea* plant In one embodiment, the invention relates to a cultivated *Brassica oleracea* plant resistant to *Albugo candida*, wherein the genetic determinant linked to *Albugo candida* resistance locus is a qualitative *Albugo candida* resistance locus.

In one further embodiment, the plant according to the present invention is a cultivated *Brassica oleracea* plant resistant to *Albugo candida* comprising a resistance locus, wherein the resistance locus is located on chromosome 2.

In one further embodiment the invention relates to a cultivated *Brassica oleracea* plant according to any of the preceding embodiments, wherein the *Albugo candida* resistance locus is genetically linked to at least one marker locus, which co-segregates with *Albugo candida* resistance trait and comprises a marker that can be identified in a PCR reaction by amplification of a DNA fragment with a pair of PCR oligonucleotide primers represented by a forward primer of SEQ ID No 1 and a reverse primer of SEQ ID No 2 or any other marker located on chromosome 2 that is statistically correlated and genetically linked to *Albugo candida* resistance trait.

The present invention also concerns a cultivated *Brassica oleracea* plant according to any of the preceding embodiments, comprising at least one allele or part thereof at a qualitative trait locus in the *Brassica oleracea* genome contributing to resistance to *Albugo candida*, which is genetically linked to at least one marker locus which co-segregates with *Albugo candida* resistance trait and comprises a marker that can be identified in a PCR reaction by amplification of a DNA fragment with a pair of PCR oligonucleotide primers represented by a forward primer of SEQ ID No 1 and a reverse primer of SEQ ID No 2, or any other marker located on chromosome 2 that is statistically correlated and genetically linked to *Albugo candida* resistance trait.

In one particular embodiment, the invention concerns a cultivated *Brassica oleracea* plant according to previous embodiments wherein primers pair amplifies a DNA fragment that comprises the at least one marker locus which co-segregates with the *Albugo candida* resistance locus.

More particularly the invention concerns cultivated *Brassica oleracea* plant according to previous embodiment wherein primers pair amplifies a DNA fragment comprising at least one SNP within the at least one marker locus which co-segregates with the *Albugo candida* resistance locus.

More particularly, the at least one SNP, within the at least one marker locus which co-segregates with the *Albugo candida* resistance locus, is selected within the group comprising:

i. a SNP A represented by a T to C nucleotide exchange at position 134 in the PCR amplified product ii. a SNP B represented by a C to T nucleotide exchange at position 108 in the PCR amplified product ii. a SNP C represented by a T to C nucleotide exchange at position 366 in the PCR amplified product.

In SNP A, C corresponds to resistant allele and T to susceptible allele.

In SNP B, T corresponds to resistant allele and C to susceptible allele.

In SNP C, C corresponds to resistant allele and T to susceptible allele.

The at least one SNP can be identified by sequencing the PCR amplification product to detect any nucleotide change. Nucleotide sequencing can be achieved by techniques known in the art such as Sanger sequencing reaction followed by capillary electrophoresis.

The at least one SNP within the at least one marker locus which co-segregates with the *Albugo candida* resistance locus can also be identified by TaqMan allelic discrimination assay. Such TaqMan assay is an allelic discrimination PCR that uses fluorescent dye-labelled probes to determine which allele is present (Livak K J, *Allelic discrimination using fluorogenic probes and the 5′ nuclease assay. Gen Anal-Biomol Eng* 14: 143-149 (1999). When DNA from a susceptible plant is tested, the VIC-labelled S-selective probe anneals to its target sequence and is then cleaved in the PCR by the 5′ nuclease activity of Taq DNA polymerase, thereby releasing the VIC dye away from its quencher and resulting in an increase in VIC fluorescence. Conversely, when DNA from a resistant plant is tested, only the FAM-labelled R-selective probe anneals, resulting in cleavage of this probe and an increase in FAM fluorescence. The relative fluorescence of these two dyes is measured in real time during the PCR, with the endpoint values corrected for background and plotted against each other in a bivariate scatter plot.

In one particular embodiment, SNP A can be identified with a SNP A can be identified with a pair of PCR oligonucleotide primers represented by a forward primer of SEQ ID No 3 and a reverse primer of SEQ ID No 4 and DNA probe of SEQ ID No 5 defining the resistant allele.

In one embodiment, the invention relates to a cultivated *Brassica oleracea* plant according to any of the previous embodiments, comprising at least one allele or part thereof at a qualitative trait locus in the *Brassica oleracea* genome contributing to resistance to *Albugo candida*, which is complementary to the corresponding allele present in *Brassica oleracea* L var *gemmifera* UK 925, seed of which is deposited under Deposit Number NCIMB 41654, or in the progeny or in an ancestor thereof, and genetically linked to at least one marker locus in the genome of *Brassica oleracea* L var *gemmifera* UK 925, seed of which is deposited under deposit Number NCIMB 41654, or in the progeny or in an ancestor thereof, which marker locus co-segregates with the *Albugo candida* resistance trait and comprises a marker that can be identified in a PCR reaction by amplification of a DNA fragment with a pair of PCR oligonucleotide primers represented by a forward primer of SEQ ID No 1 and a reverse primer primer of SEQ ID No 2, or any other marker located on chromosome 2 that is statistically correlated and genetically linked to *Albugo candida* resistance trait.

In one embodiment of the invention, a cultivated *Brassica oleracea* plant resistant to *Albugo candida* is provided, comprising a genetic determinant linked to *Albugo candida* resistance locus, wherein the genetic determinant is obtainable from a donor plant having the genetic background of *Brassica oleracea* L var *gemmifera* UK 925, seed of which is deposited under Deposit Number NCI MB 41654, or in the progeny or in an ancestor thereof, comprising said genetic determinant or an *Albugo candida* resistance-conferring part thereof.

In one particular embodiment, a cultivated *Brassica oleracea* plant according to the present invention is provided, wherein the genetic determinant provides a monogenic and dominant, or at least semi-dominant resistance to *Albugo candida*.

In one embodiment, the present invention concerns a cultivated *Brassica oleracea* plant, particularly a di-haploid, an inbred or a hybrid.

In yet another preferred embodiment, the cultivated plant according to the present invention is male sterile, particularly cytoplasmic male sterile (CMS).

The male fertility of male sterile cultivated plants can be restored by methods well-known in the art. The male fertility of CMS cultivated plants, in particular CMS *B. oleracea* cultivated plants, is preferably restored by cell fusion. For this, cells of a CMS cultivated plant are fused to cells of a male fertile cultivated plant to replace the nucleus of the fertile cultivated plant by the nucleus of sterile cultivated plant in the fertile cytoplasmic background, and restore fertility. Cell fusion techniques are well-known in the art and are for example described in Sigareva and Earle (1997) Theor. Appl. Genet. 94: 213-320. Using such techniques, male fertile cultivated plants are regenerated, and allowed to self-pollinate or crossed to another cultivated plant.

According to the present invention, seeds of cultivated *Brassica oleracea* plant according to the different embodiments represented and described herein comprising the genetic determinant contributing to resistance to *Albugo candida*, are provided.

In a particular embodiment, seed of cultivated *Brassica oleracea* plant according to the different embodiments represented and described herein is hybrid seed.

Also, the present invention concerns seeds of cultivated *Brassica oleracea* plant according to the different embodiments represented and described herein wherein the resistance locus is located on chromosome 2.

*Brassica* species and sub-species are for example described in P. H. Williams (*Screening Crucifers for multiple disease resistance, Workshop* 1981, Un. Wisconsin-Madison) and have been further genetically analyzed in Song, K M et al. (*TAG* 75, 1988, 784-794; *TAG* 76, 1988, 593-600 and *TAG* 79, 1990, 497-506. Series of 3 articles).

In a preferred embodiment, *Brassica oleracea* cultivated plants of the present invention are for example: *Brassica oleracea* L. (cole-crops) var. *acephala* DC. (kales, collards) var. *albiflora* Sun [=*B. alboglabra*] (Chinese kale) var. *alboglabra [=B. alboglabra*] (Chinese kale) var. *botrytis* L. (cauliflower, heading broccoli) var. *capitata* L. (cabbage) var. *chinensis* Prain (burma sarson) var. *fimbriata* Mill. (kitchen kale) var. *fruticosa* Metz. (thousand-head kale) var. *gemmifera* DC. (Brussels sprouts) var. *gongylodes* L. (kohlrabi) var. *italica* Plenck. (broccoli, calabrese) var. *sabauda* L. (savoy cabbage) var. *tronchuda* L. H. Bailey (tronchuda cabbage) var. *costata* (Portugese cabbage) var. *medullosa* (marrow stem kale) var. *palmifolia* (kale, Jersey kale) var. *ramosa* (thousand-head kale) var. *sabellica* (borecole). Preferred *B. oleracea* cultivated plants of the present invention are white cabbage, cauliflower, Brussels sprouts, Savoy cabbage and broccoli.

In one embodiment the present invention also provides plant material from a cultivated *Brassica oleracea* plant according to any described embodiment comprising leaves, stems, shoots, roots, flowers, flower parts, buds, florets, pollen, egg cells, zygotes, seeds, cuttings, cells or tissue cultures or any other part or product of the plant which still exhibits the resistance phenotype, particularly when grown into a plant.

In one embodiment the cultivated *Brassica oleracea* plant according to the present invention is a cultivated *Brassica oleracea* plant according to any of the preceding embodiments, which grows edible leaves, florets, buds, curds, stalk, and sprouts for human consumption.

In a further embodiment, the present invention relates to a method for producing or selecting a cultivated *Brassica oleracea* plant, exhibiting resistance to *Albugo candida*, comprising the steps of:

a. selecting a plant of the genus *Brassica*, which exhibits *Albugo candida* resistance, wherein said resistance is associated with at least one genetic determinant or a functional part thereof capable of directing or controlling expression of said resistance to *Albugo candida*, wherein said genetic determinant is genetically linked to at least one marker locus, which co-segregates with the *Albugo candida* resistance trait and comprises a marker that can be identified in a PCR reaction by amplification of a DNA fragment with a pair of PCR oligonucleotide primers represented by a forward primer of SEQ ID No 1 and a reverse primer of SEQ ID No 2, or any other marker located on chromosome 2 that is statistically correlated and genetically linked to *Albugo candida* resistance trait;
b. crossing said plant of step a), which exhibits *Albugo candida* resistance, with a *Brassica* plant, particularly a cultivated *Brassica oleracea* plant, which is susceptible to *Albugo candida* or exhibits a low level of resistance against *Albugo candida*, and
c. selecting progeny from said cross which exhibits *Albugo candida* resistance and demonstrates association with said at least one marker locus of step a).

In a particular embodiment, in the method for producing or selecting a cultivated *Brassica oleracea* plant resistant to *Albugo candida* as described above, primer pair amplifies a DNA fragment comprising at least one SNP within the at least one marker locus which co-segregates with the *Albugo candida* resistance locus.

In a further particular embodiment the at least one SNP within the at least one marker locus which segregates with the *Albugo candida* resistance locus is selected within the group comprising:

i. a SNP A represented by a T to C nucleotide exchange at position 134 in the PCR amplified product
ii. a SNP B represented by a C to T nucleotide exchange at position 108 in the PCR amplified product
ii. a SNP C represented by a T to C nucleotide exchange at position 366 in the PCR amplified product.

In SNP A, C corresponds to resistant allele and T to susceptible allele.

In SNP B, T corresponds to resistant allele and C to susceptible allele.

In SNP C, C corresponds to resistant allele and T to susceptible allele.

In an embodiment of the above selection or production method of a cultivated *Brassica oleracea* plant resistant to *Albugo candida*, the SNP A can be identified with a pair of PCR oligonucleotide primers represented by a forward primer of SEQ ID No 3 and a reverse primer of SEQ ID No 4 and a DNA probe of SEQ ID No 5 defining the resistant allele.

In a further embodiment, a method according to any one of the previous embodiments is provided for obtaining a cultivated *Brassica oleracea* plant, resistant to *Albugo candida*, wherein the donor *Brassica* plant of step (a) is a *Brassica oleracea* plant according to any embodiments of the present invention, the method comprising the additional step of backcrossing the *Albugo candida* resistant *Brassica oleracea* plant obtained in step c) with the susceptible *Brassica oleracea* plant of step b).

In one embodiment of the present invention, the determination of the association between *Albugo candida* resistance and the at least one marker locus in step c) of the method here above described is accomplished by carrying out a PCR reaction with the primers identified in step a).

The present invention also provides the use of cultivated *Brassica oleracea* plants resistant to *Albugo candida* according to the different embodiment of the present invention for the production of *Brassica oleracea* plant part for human consumption.

In one particular embodiment, the use of cultivated *Brassica oleracea* plants resistant to *Albugo candida* according to the previous embodiment comprises plant part which is selected from the group comprising: leaves, bud, florets, curd, stem.

In a further embodiment, the invention provides a method for obtaining *Brassica oleracea* edible parts resistant to *Albugo candida* comprising the steps of
  i. sowing a seed of plant according to the present invention herein described or obtained in a method as herein claimed, and
  ii. growing said plant in order to produce edible parts and harvesting the said edible parts produced by said plant.

The present invention discloses the use of *Albugo candida* resistant propagating material obtainable from a cultivated *Brassica oleracea* plant according to the present invention herein described or obtained in a method as herein claimed for growing an *Albugo candida* resistant *Brassica oleracea* plant in order to produce edible parts and harvest said edible parts.

Edible parts of a plant according to the present invention comprise leaves, sprouts, stems, stalks, curds, florets and the like of a plant according to the different embodiment of the present invention.

Edible parts of a plant according to the present invention also comprise processed, including minimally processed, part of plant such as shredded leaves, cut leaves, cut florets, cut sprouts, cut curds, cut stems and stalks.

Indeed beside the fact that *Albugo candida* induces abnormal growth and decreased yield for production of cultivated *Brassica* species, it also negatively impacts the visual appearance of the edible part of the plant. The infection by the pathogen induces white or creamy pustules filled sporangia on leaves, stems, and floral parts of the plant. All these abnormalities constitute huge drawbacks regarding commercialization of the edible part of the *Brassica oleracea* plant as definitively non-appealing regarding the consumer consideration.

Due to the resistance of the cultivated *Brassica oleracea* plant according to the present invention to *Albugo candida*, the edible part of the said plant have a much better appealing aspect for consumer. Such appealing aspect is positive either for raw or fresh market or for intermediate and fully processed products. Such intermediate processed products may comprise, without limitation, shredded cabbage in bag, broccoli florets and cauliflower curds packed fresh or frozen, for example.

The present invention also relates to the use of *Albugo candida* resistant propagating material obtainable from a *Brassica oleracea* plant according to any of the preceding embodiments for growing an *Albugo candida* resistant plant in order to produce edible parts and harvest said edible parts.

In still another embodiment, the instant invention provides a method of protecting a field of *Brassica oleracea* plants, particularly *Brassica oleracea* plants, against infection by *Albugo candida*, wherein said method is characterized by planting a seed according to the present invention herein described or obtained in a method as herein claimed, and growing a cultivated *Brassica oleracea* plant which exhibits a resistance against *Albugo candida*. In a further particular embodiment, said *Brassica* plant or field is sprayed with a crop protection chemical active against *Albugo candida* at a lower concentration or less frequently than a *Brassica oleracea* plant not exhibiting said resistance.

The present invention is particularly advantageous in that the resistance of the instant invention is easily transferred between *B. oleracea* cultivated plants and commercial lines. Higher yields are obtained because of the absence of disease on resistant cultivated plants. Moreover much less crop protection chemicals or no crop protection chemicals at all are required against *Albugo candida* when *B. oleracea* cultivated plants of the present invention are grown.

In one embodiment, the invention relates to a method for producing hybrid seeds of *Brassica*, particularly *Brassica oleracea*, resistant to *Albugo candida* comprising the steps of:
  i. planting a female, particularly a male sterile female plant, and a male plant according to any of preceding embodiments according to the present invention,
  ii. effecting cross pollination between both parents,
  iii. growing the plant till seed setting,
  iv. collecting the seeds and
  v. obtaining the hybrid seeds.

In a particular embodiment of the method of producing hybrid seeds according to the previous embodiment, the male sterile female parent is genetic male sterile (GMS) or cytoplasmic male sterile (CMS).

In another preferred embodiment, the cultivated plant according to the present invention is homozygous or heterozygous for the resistance to *Albugo candida*.

DEFINITIONS

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

A cultivated "*Brassica*" *oleracea* plant is understood within the scope of the invention to refer to a plant that is no longer in the natural state but has been developed by human care and for human use and/or consumption. "Cultivated *Brassica oleracea* plants" are further understood to exclude those wild-type species which comprise the trait being subject of this invention as a natural trait and/or part of their natural genetics.

A "genetic determinant contributing to resistance" is understood herein to refer to a heritable genetic element that is capable of contributing to the resistance of the plant towards the pathogen by influencing expression of this resistance trait on the level of the DNA itself, on the level of translation, transcription and/or activation of a final polypeptide product, i.e., to down regulate and counter the infestation leading to the phenotypic expression of the resistance.

An "allele" is understood within the scope of the invention to refer to alternative or variant forms of various genetic units identical or associated with different forms of a gene or of any kind of identifiable genetic element, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

An allele associated with a qualitative trait may comprise alternative or variant forms of various genetic units including those that are identical or associated with a single gene or multiple genes or their products or even a gene disrupting or controlled by a genetic factor contributing to the phenotype represented by the locus.

As used herein, the term "marker allele" refers to an alternative or variant form of a genetic unit as defined herein above, when used as a marker to locate genetic loci containing alleles on a chromosome that contribute to variability of phenotypic traits.

As used herein, the term "breeding", and grammatical variants thereof, refer to any process that generates a progeny individual. Breedings can be sexual or asexual, or any combination thereof. Exemplary non-limiting types of breedings include crossings, selfings, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes.

"Heterozygous" is understood within the scope of the invention to refer to unlike alleles at one or more corresponding loci on homologous chromosomes.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene or any other genetic element or factor contributing to a trait.

As used herein, "marker locus" refers to a region on a chromosome, which comprises a nucleotide or a polynucleotide sequence that is present in an individual's genome and that is associated with one or more loci of interest, which may which comprise a gene or any other genetic element or factor contributing to a trait. "Marker locus" also refers to a region on a chromosome, which comprises a polynucleotide sequence complementary to a genomic sequence, such as a sequence of a nucleic acid used as probes.

"Genetic linkage" is understood within the scope of the invention to refer to an association of characters in inheritance due to location of genes in proximity on the same chromosome, measured by percent recombination between loci (centi-Morgan, cM).

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the term "genetic architecture at the qualitative trait locus" refers to a genomic region which is statistically correlated to the phenotypic trait of interest and represents the underlying genetic basis of the phenotypic trait of interest.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants). The term "selfing" refers in some embodiments to the production of seed by self-fertilization or self-pollination; i.e., pollen and ovule are from the same plant.

As used herein, the phrase "genetic marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

A genetic marker can be physically located in a position on a chromosome that is within or outside of the genetic locus with which it is associated (i.e., is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a non-zero rate of recombination between the genetic marker and the locus of interest, the presently disclosed subject matter can also employ genetic markers that are physically within the boundaries of a genetic locus (e.g., inside a genomic sequence that corresponds to a gene such as, but not limited to a polymorphism within an intron or an exon of a gene). In some embodiments of the presently disclosed subject matter, the one or more genetic markers comprise between one and ten markers, and in some embodiments the one or more genetic markers comprise more than ten genetic markers.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest. Thus, in some embodiments a genotype comprises a summary of one or more alleles present within an individual at one or more genetic loci of a quantitative trait. In some embodiments, a genotype is expressed in terms of a haplotype (defined herein below).

As used herein, the term "germplasm" refers to the totality of the genotypes of a population or other group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geographical area, while the phrases "non-adapted germplasm," "raw germplasm," and "exotic germplasm" refer to plant materials of unknown or unproven genetic value; e.g., for a given environment or geographical area; as such, the phrase "non-adapted germplasm" refers in some embodiments to plant materials that are not part of an established breeding population and that do not have a known relationship to a member of the established breeding population.

As used herein, the terms "hybrid", "hybrid plant," and "hybrid progeny" refers to an individual produced from genetically different parents (e.g., a genetically heterozygous or mostly heterozygous individual).

As used herein, the phrase "single cross $F_1$ hybrid" refers to an $F_1$ hybrid produced from a cross between two inbred lines.

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest. An "inbred", "inbred individual" or "inbred progeny" is an individual sampled from an inbred line.

As used herein, the term "dihaploid line", refers to stable inbred lines issued from another culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially not segregating any more (stable).

As used herein, the term "linkage", and grammatical variants thereof, refers to the tendency of alleles at different loci on the same chromosome to segregate together more often than would be expected by chance if their transmission were independent, in some embodiments as a consequence of their physical proximity.

As used herein, the phrase "nucleic acid" refers to any physical string of monomer units that can be corresponded to a string of nucleotides, including a polymer of nucleotides (e.g., a typical DNA, cDNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises or encodes complementary sequences, in addition to any sequence explicitly indicated.

As used herein, the phrase "phenotypic trait" refers to the appearance or other detectable characteristic of an individual, resulting from the interaction of its genome, proteome and/or metabolome with the environment.

As used herein, the phrase "resistance" refers to the ability of a plant to restrict the growth and development of a specified pathogen and/or the damage they cause when compared to susceptible plants under similar environmental conditions and pathogen pressure. Resistant plants may exhibit some disease symptoms or damage under pathogen pressure, e.g. fungus.

According to European Seed Association and as used therein, the term "resistance" includes "standard resistance" and "intermediate resistance"

"Standard resistance" refers to plants that highly restrict the growth and development of the specified pest or pathogen under normal pest or pathogen pressure and/or are sufficiently unattractive to the specified pest or pathogen so that they exhibit no or only minor disease symptoms or damage when compared to susceptible counterparts. These plants may, however, exhibit some disease symptoms or damage under heavy pest or pathogen pressure.

"Intermediate resistance" refers to plants that distract insects and/or restrict the growth and development of the specified pest or pathogen, or show reduced damage compared to susceptible counterparts but may exhibit a greater range of symptoms or damage compared to standard resistant plants. Intermediate resistant plants will still show significantly less severe symptoms or damage than susceptible plants when grown under similar environmental conditions and/or pest or pathogen pressure As used herein, the phrase "susceptibility" refers to the inability of a plant to adequately restrict the growth and development of a specified pathogen.

As used herein, the phrase "*Albugo* resistance" or "resistance to *Albugo candida*" or "*Albugo* resistant plant" refers to the plants capability to resist colonization by the fungus. *Albugo* resistance is determined within the scope of the present invention in a pathotest as described in detail in Example 1. Particularly a plant resistant to *Albugo candida* in the context of the present invention shows a score comprised between 6 and 9 in the scale according to pathotest of Example 1.

As used herein, the term "plurality" refers to more than one. Thus, a "plurality of individuals" refers to at least two individuals. In some embodiments, the term plurality refers to more than half of the whole. For example, in some embodiments a "plurality of a population" refers to more than half the members of that population.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the phrase "qualitative trait" refers to a phenotypic trait that is controlled by one or a few genes that exhibit major phenotypic effects. Because of this, qualitative traits are typically simply inherited. Examples in plants include, but are not limited to, flower color, fruit color, and several known disease resistances such as, for example, Fungus spot resistance.

"Marker-based selection" is understood within the scope of the invention to refer to e.g. the use of genetic markers to detect one or more nucleic acids from the plant, where the nucleic acid is associated with a desired trait to identify plants that carry genes for desirable (or undesirable) traits, so that those plants can be used (or avoided) in a selective breeding program.

"Microsatellite or SSRs (Simple Sequence Repeats) Marker" is understood within the scope of the invention to refer to a type of genetic marker that consists of numerous repeats of short sequences of DNA bases, which are found at loci throughout the plant's genome and have a likelihood of being highly polymorphic.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Phenotype" is understood within the scope of the invention to refer to a distinguishable characteristic(s) of a genetically controlled trait.

As used therein "trait" refers to characteristic or phenotype, for example a resistance to a disease. A trait may be inherited in a dominant or recessive manner, or may be monogenic or polygenic. A trait is for example a resistance to a disease.

As used herein, the phrase "phenotypic trait" refers to the appearance or other detectable characteristic of an individual, resulting from the interaction of its genome, proteome and/or metabolome with the environment.

"Polymorphism" is understood within the scope of the invention to refer to the presence in a population of two or more different forms of a gene, genetic marker, or inherited trait or a gene product obtainable, for example, through alternative splicing, DNA methylation, etc.

"Selective breeding" is understood within the scope of the invention to refer to a program of breeding that uses plants that possess or display desirable traits as parents.

"Tester" plant is understood within the scope of the invention to refer to a plant of the genus *Brassica* used to characterize genetically a trait in a plant to be tested. Typically, the plant to be tested is crossed with a "tester" plant and the segregation ratio of the trait in the progeny of the cross is scored.

"Probe" as used herein refers to a group of atoms or molecules which is capable of recognising and binding to a specific target molecule or cellular structure and thus allowing detection of the target molecule or structure. Particularly, "probe" refers to a labeled DNA or RNA sequence which can be used to detect the presence of and to quantitate a complementary sequence by molecular hybridization.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point for the specific sequence at a defined ionic strength and pH. Typically, under "stringent conditions" a probe will hybridize to its target subsequence, but to no other sequences.

The thermal melting point is the temperature (under defined ionic strength and pH) at which 50% of the target sequence hybridizes to a perfectly matched probe. Very stringent conditions are selected to be equal to the T.sub.m for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2 times SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" or "plant material obtainable from a plant" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

The terms "race" or "races" refer to any inbreeding group, including taxonomic subgroups such as subspecies, taxonomically subordinate to a species and superordinate to a subrace and marked by a pre-determined profile of latent factors of hereditary traits.

As used herein, the term "population" means a genetically heterogeneous collection of plants sharing a common genetic derivation As used herein, the term "variety" or "cultivar" means a group of similar plants that by structural features and performance can be identified from other varieties within the same species.

As used therein "semi dominance" means incomplete dominance; the production of an intermediate phenotype in individuals heterozygous for the gene concerned; it is generally considered to be a type of incomplete dominance, with the heterozygote resembling one homozygote more than the other.

As used therein "dominant" means: a gene that produces the same phenotypic character when its alleles are present in a single dose (heterozygous) per nucleus, as it does in a double dose (homozygous).

As used therein "recessive" means for a gene and/or allele whose phenotypic effect is expressed in the homozygous state but masked in the presence of the dominant allele in the heterozygous state.

In one embodiment, the present invention relates to novel *Albugo candida* resistant *Brassica* plants, particularly *Brassica oleracea* plants, and lines, and improved methods for producing them utilizing the molecular markers described herein in selective breeding techniques. *Brassica* plants that do not contain at least one of the marker locus identified herein are susceptible to infection by *Albugo candida*.

In particular, the at least one marker locus controlling the *Albugo candida* resistance is located within genome of *Albugo candida* resistant *Brassica oleracea* plant. Molecular markers co-segregating with the *Albugo candida* resistance can be identified using marker-assisted selection, the techniques for which are well known in the art. Markers that can be used in such selection techniques are represented by at least one oligonucleotide primer selected from the group of primers given in SEQ ID NO:1, SEQ ID NO: 2, by any adjacent marker that is statistically correlated and thus co-segregates with the *Albugo candida* resistance trait.

In one aspect, the plant according to the present invention may be obtained by introgressing the *Albugo candida* resistance trait from an ancestor plant, particularly a wild ancestor plant into a cultivated *Brassica* plant, particularly a cultivated *Brassica oleracea* plant.

In one specific embodiment, of the invention, the wild ancestor from which *Albugo candida* resistance trait may be obtained is a wild type *Brassica oleracea*, particularly wild primitive *Brassica oleracea* acephala HRI 1205, or from an progeny or an ancestor thereof comprising said resistance trait locus.

For this accession the following source history can be provided:
Accession was collected in Portugal in 4 Oct. 1993.

Locality: Quinta da Igreja. Macainhas de baixo guarda.

Donors: UNKFARIAS ASTLEY & CHEUNG SO MUI.

Maintained by Warwick HRI Genetic Resources Unit University of Warwick, Wellesbourne, Warwick, UK.

The resistance trait according to the present invention, which confers to a plant expressing this trait, resistance to infestations with *Albugo candida*, may in the alternative, be obtained from *Brassica oleracea* L var *gemmifera* UK 925, seed of which is deposited under deposit Number NCIMB 41654.

*Brassica oleracea* L var *gemmifera* UK 925 resulted from a cross of *Brassica oleracea* acephala HRI 1205, as the donor of the resistance trait with a Brussels sprout inbred line. *Albugo* resistant progeny of this cross was further backcrossed with the recipient Brussels sprout line and then selfed several times in order to have a fixed line for resistance. The fixed line for resistance was then crossed with a female line holding CMS in order to obtain the UK 925 *Brassica oleracea* L var *gemmifera*, seed of which is deposited under deposit Number NCIMB 41654.

Moreover, other accessions of related *Brassica oleracea* species can be examined for the presence of at least one of the marker locus identified herein by using the markers of the present invention.

The molecular markers provided herein and co-segregating with at least one marker locus contributing to *Albugo candida* resistance, may be used to introgress one or more of said marker locus from a first donor plant into a second recipient plant.

Based on the description of the present invention, the skilled person who is in possession of *Brassica oleracea* L var *gemmifera* UK 925 or of an ancestor containing a trait locus associated with *Albugo candida* resistance, has no difficulty to transfer the *Albugo candida* resistance trait of the present invention to other cultivated *Brassica oleracea* plants of various type and cultivars using breeding techniques well known in the art.

Thus the trait of the present invention can be transferred to cultivated *Brassica oleracea* plant such as *Brassica oleracea* L. (cole-crops) var. *acephala* DC. (kales, collards) var. *albiflora* Sun [=*B. alboglabra*] (Chinese kale) var. *alboglabra [=B. alboglabra*] (Chinese kale) var. *botrytis* L. (cauliflower, heading broccoli) var. *capitata* L. (cabbage) var. *chinensis* Prain (burma sarson) var. *fimbriata* Mill. (kitchen kale) var. *fruticosa* Metz. (thousand-head kale) var. *gemmifera* DC. (Brussels sprouts) var. *gongylodes* L. (kohlrabi) var. *italica* Plenck. (broccoli, calabrese) var. *sabauda* L. (savoy cabbage) var. *tronchuda* L. H. Bailey (tronchuda cabbage) var. *costata* (Portugese cabbage) var. *medullosa* (marrow stem kale) var. *palmifolia* (kale, Jersey kale) var. *ramosa* (thousand-head kale) var. *sabellica* (borecole).

The recipient plant is preferably a cultivated *Brassica* plant, particularly a cultivated *Brassica oleracea*, more particularly a cultivated *Brassica oleracea* selected from the group comprising: *Brassica oleracea* L. (cole-crops) var. *acephala* DC. (kales, collards) var. *albiflora* Sun [=*B. alboglabra*] (Chinese kale) var. *alboglabra [=B. alboglabra*] (Chinese kale) var. *botrytis* L. (cauliflower, heading broccoli) var. *capitata* L. (cabbage) var. *chinensis* Prain (burma sarson) var. *fimbriata* Mill. (kitchen kale) var. *fruticosa* Metz. (thousand-head kale) var. *gemmifera* DC. (Brussels sprouts) var. *gongylodes* L. (kohlrabi) var. *italica* Plenck. (broccoli, calabrese) var. *sabauda* L. (savoy cabbage) var. *tronchuda* L. H. Bailey (tronchuda cabbage) var. *costata* (Portugese cabbage) var. *medullosa* (marrow stem kale) var. *palmifolia* (kale, Jersey kale) var. *ramosa* (thousand-head kale) var. *sabellica* (borecole). Preferred recipient *Brassica oleracea* cultivated plants of the present invention are white cabbage, cauliflower, Brussels sprouts, savoy cabbage and broccoli Cultivated *Brassica* plants developed according to the present invention can advantageously derive a majority of their traits from the recipient plant, and derive *Albugo candida* resistance from the first donor plant. According to one aspect of the present invention, genes that encode for *Albugo candida* resistance are mapped by identifying molecular markers linked to resistance qualitative trait loci, the mapping utilizing a mix of resistant and susceptible to *Albugo candida* inbred *Brassica* plants for phenotypic scoring. Molecular characterization of such lines can be conducted using the techniques described by Monforte and Tanksley in Genome, 43: 803-813 (2000).

In another embodiment of the present invention, the present invention relates to methods for producing superior new *Albugo candida* resistant *Brassica* plants. In the method of the present invention, one or more genes encoding for *Albugo candida* resistance are introgressed from a donor parental plant that is resistant to *Albugo candida* into a recipient cultivated *Brassica* plant that is either non-resistant or a plant that has a low level of resistance to infection by *Albugo candida*. The *Albugo candida* resistant cultivated *Brassica oleracea* plants according to the present embodiments of the invention or produced according to the methods of the present invention can be either inbred, hybrid, or dihaploid *Brassica* plants.

The introgression of one or more genes encoding for *Albugo candida* resistance into a recipient *Brassica* plant that is non-resistant or possesses a low level of resistance to *Albugo candida* can be accomplished using techniques known in the art. For example, one or more genes encoding for *Albugo candida* resistance can be introgressed into a recipient *Brassica oleracea* plant that is non-resistant or a plant that has a low level of resistance to *Albugo candida* using traditional breeding techniques.

The resistance to *Albugo candida* was transferred to different species of cultivated *Brassica oleraceas*, in particular white cabbage, cauliflower, broccoli and Brussels sprouts, using standard breeding techniques well-known in the *Brassica* art. The trait was also further introgressed into cultivated *Brassica oleracea* elite lines. The introgression of the resistance into the elite line can for example be achieved by recurrent selection breeding, for example by backcrossing.

In this case, the elite line (recurrent parent) is first crossed to a donor inbred (the non-recurrent parent) that carries the resistance. The progeny of this cross is then crossed back to the recurrent parent followed by selection in the resultant progeny for *Albugo candida* resistance. After two, preferably three, preferably four, more preferably five or more generations of backcrosses with the recurrent parent with selection for *Albugo candida* resistance, the progeny is heterozygous for the locus harbouring the resistance, but is like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376, incorporated herein by reference). Selection for *Albugo candida* resistance is carried out after each cross.

The cultivated *Brassica oleracea* plants according to the present invention and as described herein can be used in commercial *Brassica oleracea* seeds production. Commercial *Brassica oleracea* plants are generally hybrids produced from the cross of two parental lines (inbreds). The development of hybrids requires, in general, the development of homozygous inbred lines, the crossing of these lines, and the evaluation of the crosses.

Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes and characteristics. The new inbreds are crossed with other inbred lines and the hybrids from these crosses are evaluated to determine which of those have commercial potential. Plant breeding and hybrid development are expensive and labour and time-consuming processes. Pedigree breeding starts with the crossing of two genotypes, each of which may have one or more commercially desirable characteristics, such as, but not limited to, disease resistance, insect resistance, valuable fruit characteristics, increased yield, etc. that is lacking in the other or which complements the other. If the two original parents do not provide all the desired characteristics, other sources can be included in the breeding population in order to generate an established breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5, etc. A single cross hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid performance (hybrid vigor or heterosis), can be manifested in many polygenic traits, including increased vegetative growth and increased yield. *Brassica* plants can be easily cross-pollinated. A trait is also readily transferred from one *Brassica* plant to another plant, including *Brassica* plants of different types using conventional breeding techniques, for example to further obtain commercial lines. The introgression of a trait into the elite line is for example achieved by recurrent selection breeding, for example by backcrossing. In this case, the elite line (recurrent parent) is first crossed to a donor inbred (the non-recurrent parent) that carries the trait, particularly the "*Albugo candida* resistance" trait according to the present invention. The progeny of this cross is then mated back to the recurrent parent followed by selection in the resultant progeny for the trait. After three, preferably four, more preferably five or more generations of backcrosses with the recurrent parent with selection for the trait, particularly the "*Albugo candida* resistance" trait according to the present invention, the progeny is heterozygous for the locus harbouring the resistance, but is like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376, incorporated herein by reference). Selection for the trait is carried out after each cross. Male sterility is available in *Brassica*. In particular cytoplasmic male sterility may be used in commercial lines e.g. *Brassica oleracea* cauliflower lines.

The population can be screened in a number of different ways. First, the population can be screened using a traditional pathology disease screen. Such pathology disease screens are known in the art. Specifically, the individual plants or parts thereof can be challenged in an incubator or greenhouse with *Albugo candida* and the resulting resistant or susceptible phenotypes of each plant scored. By way of example, and not of limitation, plants can be screened in a greenhouse as follows.

First, *Brassica* seeds are planted and grown to seedlings (approximate time is 3-4 weeks) in a greenhouse—with preferably >10 plants per line are evaluated. Since Resistance is not fully expressed in the cotyledons, therefore true leaves (preferably 3-4 leaf stage) are used to inoculate plants The leaves can then be rated separately using a disease rating scale of 1-9 (1 to 5=susceptible and 6 to 9=resistant with sub levels of intermediate resistance (6-7) and standard resistance (8-9)). The scale of the disease rating depends upon the presence and the size of *Albugo candida* pustules on the leaves.

*Albugo candida* spores can be collected with a vacuum pump from ripened pustules on affected material and dry stored at −20° C. (Gilijamse et al., 2004). Sporangia were suspended in cold demi-water and stored for 2 hr at 5° C. to allow the sporangia to germinate into zoospores. The zoospores can then be sprayed onto the test plants (concentration $10^{-4}$-$10^{-5}$ zoospores/ml) in a climate chamber with 100% RH. Incubation during 10-14 days at 18-20° C. in a greenhouse after which the white pustules start to appear. Final observation is done using a 1-9 scale in which 1=plants are fully covered with large pustules, and, 9=plants are healthy without showing any symptoms. Plants scoring 1-5 on this scale are regarded as being susceptible and plants scoring 6-9 are classified as being resistant; 6-7 is regarded as intermediately resistant and 8-9 as standard resistant.

Second, marker-assisted selection can be performed using one or more of the hereinbefore described molecular markers to identify those hybrid plants that contain one or more of the genes that encode for *Albugo candida* resistance. Alternatively, marker assisted selection can be used to confirm the results obtained from the pathology screen. F2 hybrid plants exhibiting a *Albugo candida* resistant phenotype contain the requisite genes encoding for *Albugo* resistance, and possess commercially desirable characteristics, are then selected and selfed for a number of generations in order to allow for the *Brassica* plant to become increasingly inbred. This process of continued selfing and selection can be performed for five or more generations. The result of such breeding and selection is the production of lines that are genetically homogenous for the genes associated with *Albugo candida* resistance as well as other genes associated with traits of commercial interest. Alternatively, a new and superior *Albugo candida* resistant inbred *Brassica oleracea* plant line can be developed using the techniques of recurrent selection and backcrossing. In this method, *Albugo candida* resistance can be introgressed into a target recipient plant (which is called the recurrent parent) by crossing the recurrent parent with a first donor plant (which is different from the recurrent parent and referred to herein as the "non-recurrent parent"). The recurrent parent is a plant that is non-resistant or has a low level of resistance to *Albugo candida* and possesses commercially desirable characteristics, such as, but not limited to disease resistance, insect resistance, valuable agronomic characteristics, etc.

The non-recurrent parent exhibits *Albugo candida* resistance and contains one or more genes that encode for *Albugo*

*candida* resistance. The non-recurrent parent can be any plant variety or inbred line that is cross-fertile with the recurrent parent. The progeny resulting from a cross between the recurrent parent and non-recurrent parent are backcrossed to the recurrent parent. The resulting plant population is then screened. The population can be screened in a number of different ways. First, the population can be screened using a traditional pathology screen as described previously herein, particularly in EXAMPLE 1. Second, marker-assisted selection can be performed using one or more of the hereinbefore described molecular markers to identify those progeny that contain one or more of genes encoding for *Albugo candida* resistance. Alternatively, marker-assisted selection can be used to confirm the results obtained from the pathology screen. Once the appropriate selections are made, the process is repeated. The process of backcrossing to the recurrent parent and selecting for *Albugo candida* resistance is repeated for approximately five or more generations. The progeny resulting from this process are heterozygous for one or more genes that encode for *Albugo candida* resistance. The last backcross generation is then selfed in order to provide for homozygous pure breeding progeny for *Albugo candida* resistance. The *Albugo candida* resistant inbred *Brassica oleracea* lines described herein can be used in additional crossings to create *Albugo candida* resistant hybrid plants. For example, a first *Albugo candida* resistant inbred *Brassica oleracea* plant can be crossed with a second inbred *Brassica oleracea* plant possessing commercially desirable traits such as, but not limited to, disease resistance, insect resistance, desirable agronomic characteristics, etc. This second inbred *Brassica* line may or may not be resistant to *Albugo candida*. The marker-assisted selection used in the hereinbefore described methods can be made, for example, step-wise, whereby the differenti *Albugo candida* resistant genes are selected in more than one generation; or, as an alternative example, simultaneously, whereby all resistance genes are selected in the same generation. Marker-assisted selection for *Albugo candida* resistance may be done before, in conjunction with, or after testing and selection for other commercially desirable input or output traits.

There are several types of molecular markers that may be used in marker-based selection including, but not limited to, restriction fragment length polymorphism (RFLP), random amplification of polymorphic DNA (RAPD), amplified restriction fragment length polymorphism (AFLP), single sequence repeats (SSR) and single nucleotide polymorphisms SNPs.

RFLP involves the use of restriction enzymes to cut chromosomal DNA at specific short restriction sites, polymorphisms result from duplications or deletions between the sites or mutations at the restriction sites.

RAPD utilizes low stringency polymerase chain reaction (PCR) amplification with single primers of arbitrary sequence to generate strain-specific arrays of anonymous DNA fragments. The method requires only tiny DNA samples and analyses a large number of polymorphic loci.

AFLP requires digestion of cellular DNA with a restriction enzyme(s) before using PCR and selective nucleotides in the primers to amplify specific fragments. With this method, using electrophoresis techniques to visualize the obtained fragments, up to 100 polymorphic loci can be measured per primer combination and only small DNA sample are required for each test.

SSR analysis is based on DNA micro-satellites (short-repeat) sequences that are widely dispersed throughout the genome of eukaryotes, which are selectively amplified to detect variations in simple sequence repeats. Only tiny DNA samples are required for an SSR analysis. SNPs use PCR extension assays that efficiently pick up point mutations. The procedure requires little DNA per sample. One or two of the above methods may be used in a typical marker-based selection breeding program.

The most preferred method of achieving amplification of nucleotide fragments that span a polymorphic region of the plant genome employs the polymerase chain reaction ("PCR") (Mullis et al., Cold Spring Harbor Symp. Quant. Biol. 51:263 273 (1986)), using primer pairs involving a forward primer and a backward primer that are capable of hybridizing to the proximal sequences that define a polymorphism in its double-stranded form.

Alternative methods may be employed to amplify fragments, such as the "Ligase Chain Reaction" ("LCR") (Barany, Proc. Natl. Acad. Sci. (U.S.A.) 88:189 193 (1991)), which uses two pairs of oligonucleotide probes to exponentially amplify a specific target. The sequences of each pair of oligonucleotides are selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069).

A further method that may alternatively be employed is the "Oligonucleotide Ligation Assay" ("OLA") (Landegren et al., Science 241:1077 1080 (1988)). The OLA protocol uses two oligonucleotides that are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Still another method that may alternatively be employed is the "Invader Assay" that uses a structure-specific flap endonuclease (FEN) to cleave a three-dimensional complex formed by hybridization of allele-specific overlapping oligonucleotides to target DNA containing a single nucleotide polymorphism (SNP) site. Annealing of the oligonucleotide complementary to the SNP allele in the target molecule triggers the cleavage of the oligonucleotide by cleavase, a thermostable FEN. Cleavage can be detected by several different approaches. Most commonly, the cleavage product triggers a secondary cleavage reaction on a fluorescence resonance energy transfer (FRET) cassette to release a fluorescent signal. Alternatively, the cleavage can be detected directly by use of fluorescence polarization (FP) probes, or by mass spectrometry. The invasive cleavage reaction is highly specific, has a low failure rate, and can detect zeptomol quantities of target DNA. While the assay traditionally has been used to interrogate one SNP in one sample per reaction, novel chip- or bead-based approaches have been tested to make this efficient and accurate assay adaptable to multiplexing and high-throughput SNP genotyping.

Nickerson et al. have described a nucleic acid detection assay that combines attributes of PCR and OLA (Nickerson et al., Proc. Natl. Acad. Sci. (U.S.A.) 87:8923 8927 (1990)). In this method, PCR is used to achieve the exponential amplification of target DNA, which is then detected using OLA.

Schemes based on ligation of two (or more) oligonucleotides in the presence of a nucleic acid having the sequence of the resulting "di-oligonucleotide", thereby amplifying the di-oligonucleotide, are also known (Wu et al., Genomics 4:560 569 (1989)), and may be readily adapted to the purposes of the present invention.

In one embodiment, the presence or absence of an amplified DNA fragment is indicative of the presence or absence of the trait itself or of a particular allele of the trait. In one embodiment, a difference in the length or nucleotide sequence of an amplified DNA fragment is indicative of the presence of a particular allele of a trait, and thus enables to distinguish between different alleles of a trait.

In a specific embodiment of the invention simple sequence repeat (SSR) markers can be used to identify invention-relevant alleles in the parent plants and/or the ancestors thereof, as well as in the progeny plants resulting from a cross of said parent plants. Simple sequence repeats are short, repeated DNA sequences and present in the genomes of all eukaryotes and consists of several to over a hundred repeats of a given nucleotide motif.

Since the number of repeats present at a particular location in the genome often differs among plants, SSRs can be analyzed to determine the absence or presence of specific alleles.

In another embodiment of the invention SNP markers are used to identify invention-relevant alleles in the parent plants and/or the ancestors thereof, as well as in the progeny plants resulting from a cross of said parent plants In the present invention a marker or a set of two or more markers may be used represented by a pair of PCR oligonucleotide primers comprising forward primer of SEQ ID NO: 1 and reverse primer of SEQ ID NO: 2, or any adjacent marker that is statistically correlated and thus co-segregates with the *Albugo candida* resistance trait which primers lead to an amplification product in a PCR reaction exhibiting a molecular weight or a nucleotide sequence, which is essentially identical or can be considered as an allele to that of a corresponding PCR amplification product obtainable from *Brassica oleracea* L var *gemmifera* UK 925, seed of which is deposited under deposit Number NCIMB 41654 in a PCR reaction with the identical primer pair(s).

In a first step, DNA or cDNA samples are obtained from suitable plant material such as leaf tissue by extracting DNA or RNA using known techniques. Primers that flank a region containing markers within the invention-relevant qualitative trait locus disclosed herein before or within a region linked thereto, are then used to amplify the DNA sample using the polymerase chain reaction (PCR) method well-known to those skilled in the art.

Basically, the method of PCR amplification involves use of a primer or a pair of primers comprising two short oligonucleotide primer sequences flanking the DNA segment to be amplified or adapter sequences ligated to said DNA segment. Repeated cycles of heating and denaturation of the DNA are followed by annealing of the primers to their complementary sequences at low temperatures, and extension of the annealed primers with DNA polymerase. The primers hybridize to opposite strands of the DNA target sequences. Hybridization refers to annealing of complementary DNA strands, where complementary refers to the sequence of the nucleotides such that the nucleotides of one strand can bond with the nucleotides on the opposite strand to form double stranded structures. The primers are oriented so that DNA synthesis by the polymerase proceeds bidirectionally across the nucleotide sequence between the primers. This procedure effectively doubles the amount of that DNA segment in one cycle. Because the PCR products are complementary to, and capable of binding to, the primers, each successive cycle doubles the amount of DNA synthesized in the previous cycle. The result of this procedure is exponential accumulation of a specific target fragment, that is approximately 2<n>, where n is the number of cycles.

Through PCR amplification millions of copies of the DNA segment flanked by the primers are made. Differences in the number of repeated sequences or insertions or deletions in the region flanking said repeats, which are located between the flanking primers in different alleles are reflected in length variations or sequence of the amplified DNA fragments. These variations can be detected, for example, by electrophoretically separating the amplified DNA fragments on gels or by using capillary sequencer. By analyzing the gel or profile, it can be determined whether the plant contains the desired allele in a homozygous or heterozygous state or whether the desired or undesired allele is absent from the plant genome.

In the alternative, the presence or absence of the desired allele may be determined by real-time PCR using double-stranded DNA dyes or the fluorescent reporter probe method.

Marker analysis can be done early in plant development using DNA samples extracted from leaf tissue of very young plants or from seed. This allows to identify plants with a desirable genetic make-up early in the breeding cycle and to discard plants that do not contain the desired, invention-relevant alleles prior to pollination thus reducing the size of the breeding population and reducing the requirements of phenotyping.

Further, by using molecular markers, a distinction can be made between homozygous plants that carry two copies of the desired, invention-relevant allele at the *Albugo candida* resistance qualitative locus and heterozygous plants that carry only one copy and plants that do not contain any copy of the favourable allele(s).

Thus, alternative markers can therefore be developed by methods known to the skilled person and used to identify and select plants with an allele or a set of alleles of a qualitative trait locus or loci according to the present invention and as disclosed herein before.

For example, the nucleotide sequence of the amplification product obtained in PCR amplification using the a pair of PCR oligonucleotide primers comprising forward primer of SEQ ID NO: 1 and reverse primer of SEQ ID NO: 2 can be obtained by those skilled in the art and new primers or primer pairs designed based on the newly determined nucleotide sequence of the PCR amplification product. Furthermore, the markers according to the invention and disclosed herein before could be positioned on a genetic map of a cultivated *Brassica* plant, in particular species of the family *Brassica oleracea*, and known markers mapping in the same or homolog or ortholog region(s) could be used as starting point for developing new markers.

Joint-analysis of genotypic and phenotypic data can be performed using standard software known to those skilled in the art. Plant introductions and germplasm can be screened for the alleles at the corresponding *Albugo candida* resistance locus disclosed herein, based on the nucleotide sequence(s) of the marker(s) at the marker locus/loci linked to said *Albugo candida* resistance locus, and the molecular weight of the allele(s) using one or more of the techniques disclosed herein or known to those skilled in the art.

The present invention therefore also relates to an isolated nucleic acid (preferably DNA but not limited to DNA) sequence that comprises a *Albugo candida* resistance locus of the present invention, or a resistance-conferring part thereof. Thus the markers discloses may be used for the identification and isolation of one or more markers or genes from *Brassica oleracea* or other vegetable crops within the genus *Brassica* that are linked or encode *Albugo candida* resistance.

Also, in one embodiment, the present invention concerns a kit for detection of *Albugo candida* resistance locus in *Brassica oleracea*, said kit comprising a pair of PCR oligonucleotide primers able to amplify a DNA marker linked to the *Albugo candida* resistance locus.

In particular embodiment, in the said kit, the said DNA marker can be amplified in a PCR reaction by amplification of a DNA fragment with a pair of PCR oligonucleotide primers represented by a forward primer of SEQ ID No 1 and a reverse primer primer of SEQ ID No 2), and said DNA fragment comprises at least one SNP marker selected within the group comprising:
  i. a SNP A represented by a T to C nucleotide exchange at position 134 in the PCR amplified product,
  ii. a SNP B represented by a C to T nucleotide exchange at position 108 in the PCR amplified product,
  ii. a SNP C represented by a T to C nucleotide exchange at position 366 in the PCR amplified product.
  In SNP A, C corresponds to resistant allele and T to susceptible allele.
  In SNP B, T corresponds to resistant allele and C to susceptible allele.
  In SNP C, C corresponds to resistant allele and T to susceptible allele More particularly, in a kit according to the present invention, the SNP A can be identified with a pair of PCR oligonucleotide primers represented by a forward primer of SEQ ID No 3 and a reverse primer of SEQ ID No 4, and a DNA probe of SEQ ID No 5 defining the resistant allele. The present invention also provides a DNA marker that is linked to *Albugo candida* resistance locus in *Brassica oleracea* and can be identified in a PCR reaction by amplification of a DNA fragment with a pair of PCR oligonucleotide primers represented by a forward primer of SEQ ID No 1 and a reverse primer primer of SEQ ID No 2), said DNA fragment comprises at least one SNP marker selected within the group comprising:
  i. a SNP A represented by a T to C nucleotide exchange at position 134 in the PCR amplified product,
  ii. a SNP B represented by a C to T nucleotide exchange at position 108 in the PCR amplified product,
  ii. a SNP C represented by a T to C nucleotide exchange at position 366 in the PCR amplified product.

The invention also provides DNA marker wherein the SNP A can be identified with a pair of PCR oligonucleotide primers represented by a forward primer of SEQ ID No 3 and a reverse primer of SEQ ID No 4 and a DNA probe of SEQ ID No 5 defining the resistant allele.

In one embodiment, the present invention also concerns the use of a DNA marker according to the previous paragraphs for diagnostic selection of *Albugo candida* resistance locus in *Brassica oleracea* plant.

Also, the invention provides the use of DNA marker according to the previous mentioned embodiments for identification in plant the presence of *Albugo candida* resistance locus and/or for monitoring of introgression of the *Albugo candida* resistance locus in cultivated *Brassica oleracea* plant.

In one embodiment the present invention discloses *B. oleracea* plants resistant to *Albugo candida* and further resistant to clubroot, wherein the resistance to clubroot is monogenic and dominant, including seeds and materials of said plants and the progeny thereof.

The present invention thus provides cultivated *Brassica oleracea* plant resistant to *Albugo candida* according to any of the embodiments described herein further characterized in that said plant resistant to clubroot disease, wherein the resistance to clubroot is monogenic and dominant

*Brassica oleracea* plants resistant to clubroot and method for obtaining them are disclosed in EP1525317 entitled Clubroot resistant *Brassica* plants.

The present invention also discloses methods to produce *B. oleracea* plants resistant to *Albugo candida* and further resistant to clubroot, methods to transfer the clubroot resistance to clubroot susceptible or less resistant *B. oleracea* plants that are resistant to *Albugo candida*.

*Albugo candida* mainly affects leaves while and *Plasmodiophra brassicae* mainly attacks the roots of *Brassica oleracea*. It is therefore advantageous to get a *Brassica oleracea* plant having combined resistant against both pathogen in order to ensure an adequate growth of the plant from the roots to the leaves.

Higher yields may be obtained because of the absence of diseases on resistant plants. Moreover much less crop protection chemicals or no crop protection chemicals at all are required against clubroot and against *Albugo candida* when *B. oleracea* plants of the present invention are grown.

The present invention therefore discloses:

A *B. oleracea* plant resistant to clubroot disease, more particularly to clubroot disease caused by the pathogen *Plasmodiophora brassicae* and resistant to *Albugo candida*.

In a specific embodiment of the invention, the resistance to clubroot disease is monogenic and dominant.

In another preferred embodiment, the *B. oleracea* plant that has combined resistance against clubroot disease and against *Albugo candida* is broccoli, white cabbage, cauliflower, Brussels sprouts, Borecole, Savoy, or red cabbage. In another preferred embodiment, the *B. oleracea* plant is homozygous or heterozygous for the resistance to clubroot. In another preferred embodiment, the resistance to clubroot is genetically linked to a molecular marker. Preferably, the molecular marker is obtainable by PCR amplification.

The present invention further discloses:

Seed of a *Brassica oleracea* plant which is resistant to *Albugo candida* and resistant to clubroot disease, including the progeny thereof, wherein said seed or progeny comprises the resistances of the present invention.

In another preferred embodiment, said resistance to clubroot is monogenic, preferably monogenic and dominant. In a preferred embodiment, the *B. oleracea* plant is homozygous for the clubroot resistance. In another preferred embodiment, the *B. oleracea* plant is heterozygous for the clubroot resistance.

The present invention further discloses:

Seed of a plant disclosed above, including the progeny thereof, wherein said seed or progeny comprises the resistances against *Albugo candida* and clubroot according to the present invention.

The present invention further discloses:

A method for producing a *B. oleracea* plant resistant to *Albugo candida* further comprising a monogenic and dominant resistance to clubroot comprising the steps of:
a) providing a *Brassica oleracea* resistant to *Albugo candida,*
b) obtaining a *B. rapa* plant resistant to clubroot, c) crossing said *B. rapa* plant with the *B. oleracea* plant resistant to *Albugo candida*, d) rescuing embryos resulting from the cross of step c), e) regenerating a plant from a embryo of step d), f) selecting a plant of step e) that is resistant to clubroot and resistant to *Albugo candida*, g) back-crossing a plant resulting from step f) with a *B. oleracea* plant resistant to *Albugo candida*.

In a preferred embodiment, the method further comprises introgressing the resistance into an elite *B. oleracea* inbred that is resistant to *Albugo candida*. In another preferred embodiment, the method further comprises crossing said inbred to another *B. oleracea* inbred to produce a hybrid The foregoing description will be more fully understood with the reference to the following Examples. Such Examples are, however, exemplary methods of practising the present invention and are not intended to limit the scope of the invention.

The following Examples illustrate the invention:

EXAMPLE 1

Disease Tests Used to Test for the Presence of the Resistance

Resistance is not fully expressed in the cotyledons and therefore true leaves (preferably 3-4 leaf stage) are used to inoculate plants. Plants are sown in regular peat soil in the greenhouse in trays. After 7-10 days after sowing, the seedlings are transplanted in 9×9×8 cm pots filled with regular peat soil and grown for 3-4 weeks in a greenhouse at moderate temperatures (18-20° C., night-day). When the first 3-4 leaves are fully grown, the plants can be inoculated.

Spores were collected with a vacuum pump from ripened pustules and dry stored at −20° C. (Gilijamse et al., 2004). Sporangia were suspended in cold demi-water and stored for 2 hr at 5° C. to allow the sporangia to germinate into zoospores. The zoospores were then sprayed onto the test plants (concentration $10^{-4}$-$10^{-5}$ zoospores/ml) in a climate chamber with 100% RH. Incubation during 10-14 d at 18-20° C. in a greenhouse after which the white pustules start to appear. Final observation is done using a 1-9 scale in which 1=plants are fully covered with large pustules, and, 9=plants are healthy without showing any symptoms (Table 1). Plants scoring 1-5 on this scale are regarded as being susceptible and plants scoring 6-9 are classified as being resistant; 6-7 is regarded as intermediately resistant and 8-9 as standard resistant.

TABLE 1

Scale for scoring resistance against *Albugo candida*

| scale | S/R | Nb pustules | % leaf covered with pustules |
|---|---|---|---|
| 1 | S | >50 large pustules | >80% |
| 2 | S | 30-50 large pustules | 50-80% |
| 3 | S | 15-30 large pustules | 20-50% |
| 4 | S | 5-15 large pustules | 5-20% |
| 5 | S | 1-5 large pustules and/or >20 small pustules | 1-5% |
| 6 | R | 5-20 small pustules | 0.1-1% |
| 7 | R | 1-5 small pustules | <0.1% |
| 8 | R | no pustules, only HR | 0% |
| 9 | R | no symptoms | 0% |

S = susceptible,
R = resistant

EXAMPLE 2

Transfer of the *Albugo candida* Resistance to *B. oleracea*

In 2001, individual plants of a Portuguese kale (HRI accession 12105, wild *Brassica oleracea* acephala; Couve Galega Frisada) were identified to have resistance against *Albugo candida*. These plants were selfed to fixate the resistance and then further back crossed with elite lines of cabbage, B. sprouts, cauliflower and broccoli to introgress the resistance.

In Brussels sprouts, a parental line 1 was converted with *Albugo candida* resistance by crossing with HRI 12105. After 3 generations of back crosses the B3 segregated nicely 1:1 (Table 1, pool of 2 lines). After 4 inbreeding cycles (B3F4) a near isogenic line (resembling phenotypically to Brussels sprouts parental line 1) was obtained with *Albugo candida* resistance. This line was 100% resistant. Two test crosses were made, one gave 100% resistant plants the other 97% resistant plants.

This 100% resistant line was then crossed with a female line holding CMS in order to obtain the UK 925 *Brassica oleracea* L var *gemmifera*, seed of which is deposited under deposit Number NCIMB 41654.

In another recurrent background line of Brussels sprouts, the B1 segregated also nicely into 1:1 (Table 1).

Using a white cabbage background, a B1 revealed 1:1 segregation, a fixated line showed 100% resistance as did the test F1. A B0 and B1 in cauliflower segregated 1:1.

These examples are indicative for many more backcrosses in Brussels sprouts, cabbage, Savoy cabbage, broccoli and other cultivated *Brassica oleracea* crops. Classifying the back crosses in Table 1, a S:R=1:1 segregation is present (Chi-square, P>0.05) indicative for a single (semi-)dominant gene. The data also show that introgression into different crops is possible in order to establish *Albugo candida* resistance in different cultivated *Brassica oleracea* species such as Broccoli, cauliflower, white cabbage, savoy cabbage and Brussels sprouts.

TABLE 2

Disease results of back cross programs in Brussels sprouts (BS) and white cabbage (WC).

| Plant | generation | S | R | % S | % R | Mean Score |
|---|---|---|---|---|---|---|
| Parental line 1 (BS) | F12 | 48 | 0 | 100 | 0 | 4.9 |
| Parental line 1 with *Albugo candida* resistance | B3F4 | 0 | 48 | 0 | 100 | 8.1 |
| Parent line (WC) | F10 | 15 | 0 | 100 | 0 | 3.9 |
| Fixated line with *Albugo candida* resistance | B4F3 | 0 | 24 | 0 | 100 | 8.0 |
| Test F1 | F1 | 0 | 24 | 0 | 100 | 7.8 |

Abrev:

S = susceptible,

R = resistant (score 6-9, see Table 1).

BS = Brussels sprouts,

WC = White cabbage;

Mean = mean of *Albugo candida* score (according Table 1).

Similar experiments were done with Cauliflower and Broccoli and showed that introgression of the *Albugo candida* resistance trait can be achieved by crossing and back-crossing with resistance source in order to select and produce cultivated *Brassica oleracea* plants with resistance to *Albugo candida* resistance.

EXAMPLE 3

Molecular Marker Development

Near isogenic lines (NILs) of white cabbage and Brussels sprouts with introgression from HRI1215 *Albugo candida* resistance gene were used for identification of Molecular Markers linked to resistance to *Albugo candida* disease.

To identify new markers linked to *Albugo candida* resistance from HR11215, DNA of the near-isogenic lines (NILs) derived from a B3F3 were hybridized to the *Brassica* affymetrix array. The *Arabidopsis* homologs of candidate SFP with significantly different hybridization signals between the resistant and susceptible NILs. The genomic positions of the *Arabidopsis* homologs for a large number of candidates were clustered in a block of chromosome 5 that is syntenic to the region of *B. oleracea* chromosome 2 where *Albugo candida* resistance is located. These candidates were sequenced on a trait-specific panel of fixed resistant and susceptible lines to identify polymorphisms for Taqman assay development. A homolog of At5g17610 carried SNP polymorphisms that correlated with segregation for resistance in both Brussels sprouts and cabbage.

PCR Sequencing for SNP A, SNP B and SNP C.

```
Forward primer
                                          (SEQ No 1)
5' CACGACGTTGTAAAACGACAAGAGAATTGTGCGCTGC 3'

Reverse primer
                                          (SEQ No 2)
5' CAGGAAACAGCTATGACCAAAAGCTGCCACGAACAC 3'
```

The set of primers amplify a sequence that contains SNPs at positions 108 (SNP A), 134 (SNP B), and 366 (SNP C). The resistant and susceptible samples were genotyped by sequencing the PCR products obtained by the set of primers. The sequencing was done using a Sanger sequencing reaction followed by capillary electrophoresis.

Testing a verification panel thus revealed that the following SNPs cosegregate with the resistance:

SNP A shows resistant allele with a C for T substitution at position 134 in the amplified product; C corresponding to resistant.

SNP B shows resistant allele with a T for C substitution at position 108 in the amplified product; T corresponding to resistant.

SNP C shows resistant allele with a C for T substitution at position 366 in the amplified product; C corresponding to resistant.

TaqMan Assay for SNP A

Taqman assay protocol has been developed to detect resistance to *Albugo candida* (white blister) introgressed from HR11215. This codominant assay can be applied in *Brassica oleracea* breeding for the transfer and selection of *Albugo candida* resistance in broccoli, cauliflower, cabbage, Brussels sprouts, and bore kale For SNP A a TaqMan assay was developed in order to allows a quicker determination of resistant vs susceptible individuals.

The linkage distance between the SNP A assay and the resistance locus was estimated as 1.5 cM. The locus was mapped on chromosome 2.

```
Forward primer
                                          (SEQ No 3)
5' CACCATCTAGGCTCTCCCCGAGC 3'

Reverse primer
                                          (SEQ No 4)
5' GGAGCCAAGAATACAAATATTGTATGTAC 3'
```

Probes:

```
                                          (SEQ No 5)
FAM - TCATGTTTCGTCCTAGTATAC - MGB - NFQ >
Resistant specific (SEQ No 6)
VIC - CTAATCATGTTTCGTTCTTC - MGB - NFQ >
Susceptible specific
```

Assay Conditions

1. Isolate genomic DNA with standard DNA isolation protocol (Potassium acetate) and resuspend in 100 µL of TE;
2. Dilute template DNA to 1/30;
3. Pipette 4 µL of each diluted DNA sample into individual wells;
4. Cover and centrifuge the plate and place on ice;
5. Make the mix the master mix

| Sigma protocol | Volume (µL) | Initial concentration | Final concentration |
|---|---|---|---|
| gDNA | 4.00 | | |
| Buffer 10x (Sigma) | 1.00 | 10 X | 1X |
| $MgCl_2$ | 1.20 | 25 mM | 3 mM |
| dNTP (2.5 mM each = 10 mM all) | 0.80 | 2.5 mM each | 0.2 mM each |
| Sigma Taq | 0.132 | 2.5 U/µL | 0.033 U/µl |
| HiNK12509 = SO0005AA1FM | 0.10 | 10 µM | 100 nM |
| HiNK12508 = SO0005AA2VC | 0.10 | 10 µM | 100 nM |
| HiNK12506 = SO0005AF1 | 0.45 | 10 µM | 450 nM |
| HiNK12507 = SO0005AR1 | 0.45 | 10 µM | 450 nM |
| ROX | 0.10 | 50X | 0.5X |
| $H_2O$ QSP | 1.668 | | |
| Total Volume | 10.00 | | |

6. Load the plate on PCR machine;
7. PCR program (on ABI Geneamp PCR 9700-384 plate format) as follows:

| | |
|---|---|
| 2 min 94° C. for Sigma Taq Polymerase | |
| 15 sec 94° C. | 40X |
| 1 min 60° C. | 40X |
| 5 min 72° C. | |

8. Read the plate on ABI7900.

DEPOSIT

The following seed sample of *Brassica oleracea* L var *gemmifera* was deposited with NCIMB, Ferguson Building, Craibstone Estate, bucksbum, Aberdeen AB21 9YA, Scotland, UK, on Sep. 16, 2009 under the provisions of the Budapest Treaty in the name of Syngenta Participations AG:

UK 925, deposit Number NCIMB 41654, deposition date 16 Sep. 2009.

What is claimed is:

1. Cultivated *Brassica oleracea* plant resistant to *Albugo candida*, comprising a resistance locus, such resistance locus being present in *Brassica oleracea* L var *gemmifera* UK 925, seed of which is deposited under Deposit Number NCIMB 41654, and wherein said resistance locus is a monogenic and semi-dominant resistance locus located on chromosome 2, and wherein the *Albugo candida* resistance locus is genetically linked to at least one marker locus, which co-segregates with *Albugo candida* resistance trait and comprises a marker that can be identified in a PCR reaction by amplification of a DNA fragment with a pair of PCR oligonucleotide primers represented by a forward primer of SEQ ID NO: 1 and a reverse primer of SEQ ID NO: 2.

2. Cultivated *Brassica oleracea* plant resistant to *Albugo candida* according to claim 1, wherein the resistance locus is a qualitative *Albugo candida* resistance locus.

3. Cultivated *Brassica oleracea* plant according to claim 1 wherein the primer pair amplifies a DNA fragment that comprises the at least one marker locus which co-segregates with the *Albugo candida* resistance locus.

4. Cultivated *Brassica oleracea* plant according to claim 3 wherein primer pair amplifies a DNA fragment comprising at least one SNP within the at least one marker locus which co-segregates with the *Albugo candida* resistance locus.

5. Cultivated *Brassica oleracea* plant according to claim 4 wherein the at least one SNP is selected from the group consisting of:
   i. a SNP A represented by a T to C nucleotide exchange at position 134 in the PCR amplified product
   ii. a SNP B represented by a C to T nucleotide exchange at position 108 in the PCR amplified product; and
   iii. a SNP C represented by a T to C nucleotide exchange at position 366 in the PCR amplified product.

6. Cultivated *Brassica oleracea* plant according to claim 5 wherein the SNP A can be identified with a pair of PCR oligonucleotide primers represented by a forward primer of SEQ ID NO: 3 and a reverse primer of SEQ ID NO: 4 and DNA probe of SEQ ID NO: 5 defining the resistant allele.

7. Seed of cultivated *Brassica oleracea* plant according to claim 1 comprising the resistance locus contributing to resistance to *Albugo candida*.

8. Method for producing a cultivated *Brassica oleracea* plant, exhibiting resistance to *Albugo candida*, comprising the steps of:
   a. crossing the plant of claim 1 with a cultivated *Brassica oleracea* plant, which is susceptible to *Albugo candida* or exhibits a low level of resistance against *Albugo candida*, and
   b. selecting progeny from said cross which exhibits *Albugo candida* resistance and demonstrates association with said at least one marker locus.

9. Method according to claim 8, wherein the primer pair amplifies a DNA fragment comprising at least one SNP within the at least one marker locus which co-segregates with the *Albugo candida* resistance locus.

10. Method according to claim 9, wherein the at least one SNP is selected from the group consisting of:
    i. a SNP A represented by a T to C nucleotide exchange at position 134 in the PCR amplified product
    ii. a SNP B represented by a C to T nucleotide exchange at position 108 in the PCR amplified product; and
    iii. a SNP C represented by a T to C nucleotide exchange at position 366 in the PCR amplified product.

11. Method for obtaining cultivated *Brassica oleracea* edible parts resistant to *Albugo candida* comprising the steps of
    i. sowing a seed of cultivated *Brassica oleracea* according to claim 7,
    ii. growing said plant in order to produce edible parts and harvesting the said edible parts produced by said plant.

12. Method of protecting a field of cultivated *Brassica oleracea* plants against infection by *Albugo candida*, wherein said method is characterized by planting a seed according to claim 7.

13. Method of producing hybrid seeds of a cultivated *Brassica oleracea* resistant to *Albugo candida* comprising the steps of:
    i. planting a female *Brassica oleracea* plant, and the male plant according to claim 1,
    ii. effecting cross pollination between both parents,
    iii. growing the plant till seed setting,
    iv. collecting seeds, and
    v. obtaining the hybrid seeds.

* * * * *

SEQUENCE LISTING

<160> NUMBER OF SEQ ID NOS: 6

<210> SEQ ID NO 1
<211> LENGTH: 37
<212> TYPE: DNA
<213> ORGANISM: Artificial
<220> FEATURE:
<223> OTHER INFORMATION: Forward primer

<400> SEQUENCE: 1
cacgacgttg taaaacgaca agagaattgt gcgctgc                              37

<210> SEQ ID NO 2
<211> LENGTH: 36
<212> TYPE: DNA
<213> ORGANISM: Artificial
<220> FEATURE:
<223> OTHER INFORMATION: Reverse primer

<400> SEQUENCE: 2
caggaaacag ctatgaccaa aagctgccac gaacac                               36

<210> SEQ ID NO 3
<211> LENGTH: 23
<212> TYPE: DNA
<213> ORGANISM: Artificial
<220> FEATURE:
<223> OTHER INFORMATION: Forward primer

<400> SEQUENCE: 3
caccatctag gctctccccg agc                                             23

<210> SEQ ID NO 4
<211> LENGTH: 29
<212> TYPE: DNA
<213> ORGANISM: Artificial
<220> FEATURE:
<223> OTHER INFORMATION: Reverse primer

<400> SEQUENCE: 4
ggagccaaga atacaaatat tgtatgtac                                       29

<210> SEQ ID NO 5
<211> LENGTH: 21
<212> TYPE: DNA
<213> ORGANISM: Artificial
<220> FEATURE:
<223> OTHER INFORMATION: Resistant specific probe

<400> SEQUENCE: 5
tcatgtttcg tcctagtata c                                               21

<210> SEQ ID NO 6
<211> LENGTH: 20
<212> TYPE: DNA
<213> ORGANISM: Artificial
<220> FEATURE:
<223> OTHER INFORMATION: Susceptible specific probe

<400> SEQUENCE: 6
ctaatcatgt ttcgttcttc                                                 20